(12) United States Patent
Ryu et al.

(10) Patent No.: US 12,213,711 B2
(45) Date of Patent: *Feb. 4, 2025

(54) FOUR CORNER FUSION DEVICE

(71) Applicant: OsteoMed LLC, Addison, TX (US)

(72) Inventors: Jaiyoung Ryu, Morgantown, WV (US); Terry Whipple, Richmond, VA (US); Benjamin Carl Casey, Dallas, TX (US)

(73) Assignee: OsteoMed LLC, Addison, TX (US)

( * ) Notice: Subject to any disclaimer, the term of this patent is extended or adjusted under 35 U.S.C. 154(b) by 66 days.

This patent is subject to a terminal disclaimer.

(21) Appl. No.: 17/985,606

(22) Filed: Nov. 11, 2022

(65) Prior Publication Data

US 2023/0072360 A1 Mar. 9, 2023

Related U.S. Application Data

(63) Continuation of application No. 16/796,866, filed on Feb. 20, 2020, now Pat. No. 11,497,537, which is a continuation of application No. 15/689,957, filed on Aug. 29, 2017, now Pat. No. 10,653,468.

(60) Provisional application No. 62/380,853, filed on Aug. 29, 2016.

(51) Int. Cl.
*A61B 17/80* (2006.01)
(52) U.S. Cl.
CPC .......... *A61B 17/8061* (2013.01); *A61B 17/80* (2013.01); *A61B 17/8057* (2013.01)

(58) Field of Classification Search
CPC . A61B 17/80; A61B 17/8014; A61B 17/8033; A61B 17/8052; A61B 17/8057; A61B 17/8061
See application file for complete search history.

(56) References Cited

U.S. PATENT DOCUMENTS

| | | | | |
|---|---|---|---|---|
| 5,853,413 A * | 12/1998 | Carter | ................ | A61B 17/8061 606/281 |
| 6,179,839 B1 * | 1/2001 | Weiss | ................. | A61B 17/8061 606/85 |
| 6,221,073 B1 * | 4/2001 | Weiss | ................. | A61B 17/8061 606/281 |
| 8,992,587 B2 * | 3/2015 | Kirschman | ........ | A61B 17/7064 606/305 |
| 9,717,599 B1 * | 8/2017 | Gorelick | ............... | A61F 2/4261 |
| 10,653,468 B2 * | 5/2020 | Ryu | ................... | A61B 17/8057 |
| 11,497,537 B2 * | 11/2022 | Ryu | ................... | A61B 17/8061 |
| 2002/0183754 A1 * | 12/2002 | Michelson | ......... | A61B 17/8004 606/70 |

(Continued)

*Primary Examiner* — Eric S Gibson
(74) *Attorney, Agent, or Firm* — K&L Gates LLP

(57) ABSTRACT

A method, system, and apparatus for bone fusion. Bone fusion can be performed using an elongated plate having a top face and a bottom face and defining a plurality of screw apertures therethrough. The elongated plate has a longitudinal dimension between a first and second ends and a lateral dimension between first and second sides. The screw apertures are defined in a generally straight line along the longitudinal dimension of the elongated plate, and three or more of the screw apertures are configured to facilitate different trajectories of bone screws through each of the three or more screw apertures. The screw apertures are configured to facilitate trajectories of bone screws to secure at least three bones to the elongated plate.

20 Claims, 5 Drawing Sheets

(56) References Cited

U.S. PATENT DOCUMENTS

| | | | |
|---|---|---|---|
| 2004/0127901 A1* | 7/2004 | Huebner | A61B 17/8061 606/907 |
| 2006/0025772 A1* | 2/2006 | Leibel | A61B 17/1686 606/915 |
| 2006/0036330 A1* | 2/2006 | Shultz | A61F 2/4261 623/21.12 |
| 2006/0089648 A1* | 4/2006 | Masini | A61B 17/1615 606/291 |
| 2006/0149249 A1* | 7/2006 | Mathoulin | A61B 17/8061 606/915 |
| 2007/0233123 A1* | 10/2007 | Ahmad | A61B 17/864 606/307 |
| 2011/0009866 A1* | 1/2011 | Johnson | A61B 17/8057 606/70 |
| 2012/0022603 A1* | 1/2012 | Kirschman | A61B 17/863 606/305 |
| 2012/0136453 A1* | 5/2012 | Scheker | A61F 2/4261 623/21.12 |
| 2012/0197261 A1* | 8/2012 | Rocci | A61B 17/1686 606/96 |
| 2012/0197311 A1* | 8/2012 | Kirschman | A61B 17/7098 606/104 |
| 2012/0245643 A1* | 9/2012 | Impellizzeri | A61B 17/8085 606/283 |
| 2013/0165979 A1* | 6/2013 | Greenberg | A61B 17/8061 606/280 |
| 2013/0211459 A1* | 8/2013 | Horan | A61B 17/8061 606/280 |
| 2015/0094722 A1* | 4/2015 | Champagne | A61B 17/7291 606/64 |
| 2016/0166294 A1* | 6/2016 | Schneider | A61L 27/18 606/286 |
| 2018/0055549 A1* | 3/2018 | Ryu | A61B 17/1728 |
| 2020/0187999 A1* | 6/2020 | Ryu | A61B 17/1728 |
| 2023/0072360 A1* | 3/2023 | Ryu | A61B 17/8057 |

* cited by examiner

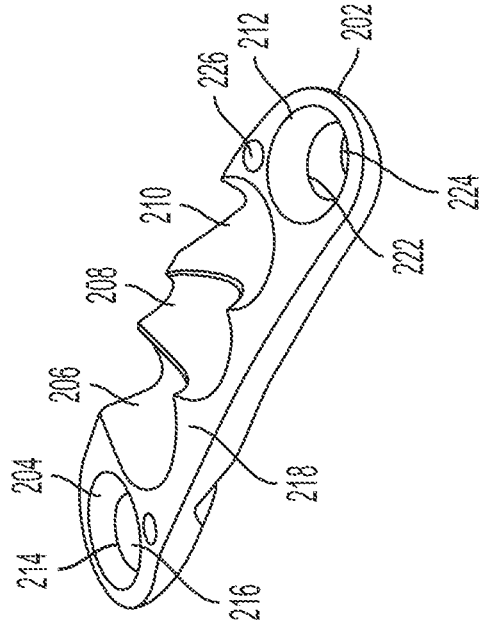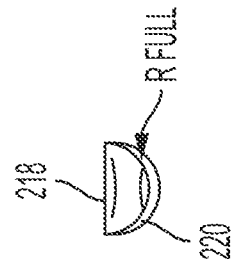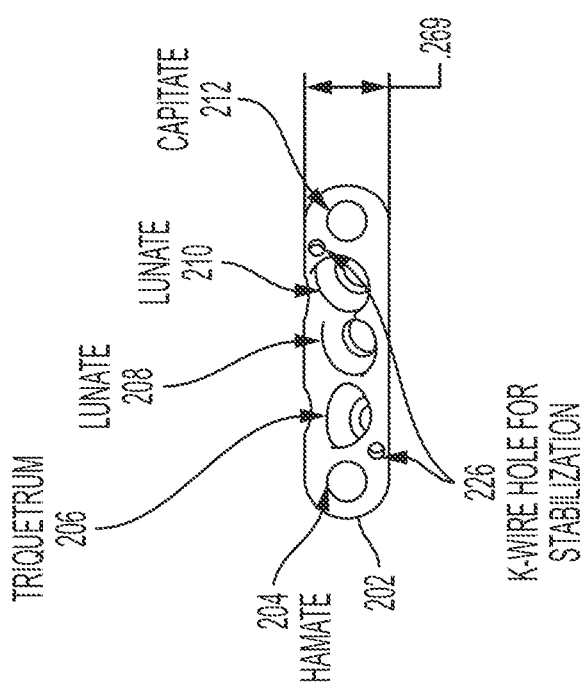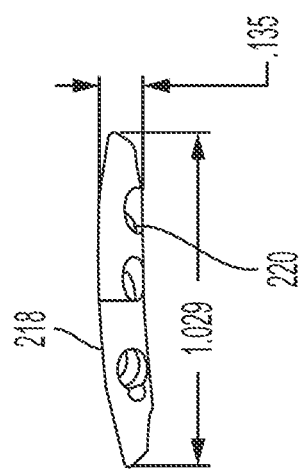

FOUR CORNER FUSION DEVICE

CROSS-REFERENCE TO RELATED APPLICATION

The present application is a continuation of U.S. patent application Ser. No. 16/796,866, filed Feb. 20, 2020 and entitled "FOUR CORNER FUSION DEVICE," which is a continuation of U.S. patent application Ser. No. 15/689,957, filed Aug. 29, 2017 and entitled "FOUR CORNER FUSION DEVICE," which issued as U.S. Pat. No. 10,653,468 on May 19, 2020, which claims priority to U.S. Provisional Patent Application No. 62/380,853, filed Aug. 29, 2016 and entitled "FOUR CORNER FUSION DEVICE," the disclosures of each of which are incorporated herein by reference in their entirety.

FIELD OF THE INVENTION

This application relates to devices, and methods of making/using devices for orthopedic surgery, and more particularly to a four corner bone fixation device for implantation within a patient's body to fixedly position multiple bones relative to one another.

BACKGROUND

Fusion of damaged or degenerated bones in joints is common in the orthopedic field. Joint fusion involves fixing two or more bones relative to one another so that they no longer move relative to one another. Joint fusion can be accomplished by securing the bones that are to be fused together using some type of appliance. In some cases, bones may simply be secured together using screws, while in other cases a plate or another appliance is used to stabilize the bones during the fusion process. Joint fusion may also involve packing bone graft material (e.g., fragments of bone removed from another location in the patient's body) between the bones of interest to facilitate a fusion process.

Joint fusion may be performed as a treatment for certain types of arthritis. For example, if arthritis of the wrist does not respond to other treatments, such as anti-inflammatory medication, application of splints, or steroid injections, a total wrist fusion may be performed in which the radius, most or all of the carpal bones, and one or more of the metacarpals are fused. However, total wrist fusion substantially diminishes function as it immobilizes virtually the entire wrist joint. Although total wrist fusion may be necessary to relieve chronic and severe pain from certain forms of arthritis, it is typically preferable to maintain as much natural motion of the wrist joint as possible.

Accordingly, limited wrist fusion may be the preferred treatment for certain types of arthritis. In limited wrist fusion, at least some of the bones of the carpus are fused together without fusing the metacarpals to the carpals or the radius to the carpals. One common limited wrist fusion procedure for patients with advanced degenerative change in the wrist is known as "four corner" fusion. Four corner fusion involves fusing the capitate, hamate, lunate, and triquetrum bones in the carpus to reduce pain from the joint while still preserving some motion. Four corner fusion may be used, for example, to treat scapholunate advanced collapse (SLAC wrist) or scaphoid nonunion advanced collapse (SNAC wrist). Four corner fusion may also be used to treat other conditions, such as trans-scaphoid perilunate fracture dislocation.

Four corner fusion may be performed simply using screws to secure the capitate, hamate, lunate, and triquetrum bones together. Overall stability can be improved, however, using an appliance that is secured to the carpus bones using screws. Moreover, such an appliance can serve as a guide for appropriate placement of screws, which can make the procedure easier to perform.

One appliance for use in four corner fusion is disclosed in U.S. Pat. No. 6,179,839 B1, issued to Weiss and Collins. The '839 patent discloses a four corner fusion apparatus that comprises an annular plate with a substantially conical shape having a top outer edge of greater diameter and a smaller diameter inner bottom edge. A conical burr is used to rasp out a conical cavity at the juncture of the capitate, hamate, lunate, and triquetrum bones. The conical, annular plate is then placed in the resulting conical cavity and bone screws are inserted through apertures in the plate into the capitate, hamate, lunate, and triquetrum bones and tightened to pull the bones together.

Another appliance for use in four corner fusion is disclosed in U.S. Patent Publication No. 2006/0025772, filed by Leibel, Cooney, Linscheid, and Berger. The '772 publication discloses a carpal compression plate for use in four corner fusion. The carpal compression plate has a concave profile and a diamond shape, and is described as having a low profile that reduces the amount of bone resection relative to the appliance disclosed in the '839 patent. The plate includes four screw apertures, at least one of which is elongate and is narrower at a peripheral end and countersunk or otherwise shaped to be broader at a central end. As one or more the screws are tightened into the elongated screw apertures, they tend to migrate from the more peripheral portion of the elongated aperture to the more central portion, drawing the bones attached to these screws to be fused tightly together. In addition, a multi-lobate central aperture is intended to provide ease of access to the joint space between the capitate, hamate, lunate, and triquetrum bones after fixation of the fusion plate to allow easier placement of bone graft.

SUMMARY

The present application describes an elongated plate for use in bone fusion. The elongated plate defines multiple screw apertures arranged in a generally straight line along a longitudinal dimension of the elongated plate between a first end and a second end of the elongated plate. The screw apertures of the elongated plate can establish a trajectory for bone screws that pass through the elongated plate and into a corresponding bone. In particular, the trajectory of the bone screws can be defined by the screw apertures of the elongated plate such that the bone screws can be secured to different bones.

The elongated plate can be used for performing four corner fusion procedures to fuse the capitate, hamate, lunate, and triquetrum bones in the carpus. In particular, different screw apertures in the elongated plate can define a trajectory corresponding to each of the capitate, hamate, lunate, and triquetrum bones. Bone screws inserted through the screw apertures can thus secure the carpus bones in a fixed position relative to one another and relative to the elongated plate.

In some embodiments, to implant the elongated plate, a channel may be cut into the bone surface of at least a subset of the bones to be fused. The elongated plate is inserted into the channel, and pilot holes may be drilled into the bone according to a trajectory defined, at least in part, by the screw apertures. Bone screws are inserted through the screw apertures and into the drilled pilot holes in the bone and are tightened to secure the bones in a fixed position. Bone graft may be placed between the bones before tightening the screws to promote bone fusion.

In some embodiments, the elongated plate may be included as part of a bone fusion kit. The kit may include the bone screws, Kirschner wires (K-wires) for use in establishing the location and trajectory for the bone screws, and a cannulated drill bit for drilling pilot holes in bone (over the K-wires) for accepting the bone screws. The kit may also include a burr for cutting an appropriately shaped channel in the bone according to the shape of the bottom face of the elongated plate. For example, the burr may be shaped to cut a concave linear channel, and the elongated plate may be shaped as a longitudinal bar with a convex bottom face along the lateral dimension. The kit may further include a bone preparation guide that can be placed on the bone to provide a guide for the location of the channel. The kit may also include one or more drill guides for limiting the angulation of the K-wires and/or the cannulated drill bit relative to the screw apertures in the elongated plate.

The bone fusion apparatus and system described in this application may provide one or more of the following advantages. The elongated plate may have a relatively small lateral dimension that limits the amount of bone resection required for implantation of the elongated plate. Limiting the amount of bone resection may improve the amount of purchase for the bone screws and avoid weakening the bones. The elongated plate may also avoid a need to resect portions of each of the capitate, hamate, lunate, and triquetrum bones by limiting the resection to just one or two of the bones (e.g., the capitate and hamate bones). The elongated plate, after it is put in position (e.g., before tightening the bone screws), can provide improved access to the fusion site. Thus, a surgeon may have better access to the joint spaces between the capitate, hamate, lunate, and triquetrum bones for insertion of bone graft. The elongated plate may also provide a common structural member to anchor all of the bones and provide a guide for the placement and trajectory of screws. The system may incorporate locking screws, which facilitates improved stability of implants by keeping the screw in place when placed under tension and thus contributes to better success of fusion. The system also may use cannulated screws, which allows insertion of K-wires to assess where a screw is going before drilling a pilot hole for the screw in the bone and inserting a bone screw. The system may enable a limited variation in the angulation of screws while simultaneously preventing undesirable angulations. A bone preparation guide can help ensure proper placement of a channel for implantation of the elongated plate. The bone fusion system allows for limited wrist fusion. The elongated plate may include physical features to prevent soft tissue from impinging on the implant. The system provides features that may be useful in bone fusion other than four corner fusion of the wrist, including at least three corner fusion, and fusion of bones in the tarsus.

DESCRIPTION OF DRAWINGS

FIGS. 2A, 2B, 2C, and 2D are a perspective view, a top plan view, a side view, and an end view, respectively, of an alternative embodiment of a four corner fusion plate.

Like reference symbols in the various drawings indicate like elements.

DETAILED DESCRIPTION

In accordance with aspects described in this application, a bone fusion appliance is formed as an elongated plate defining apertures arranged in a generally straight line along a longitudinal dimension of the elongate plate. The apertures have dimensions and have a directional orientation such that bone screws inserted through the apertures can be secured to different bones to fix the bones in a desired relative position and to facilitate fusion of the bones. The dimensions and directional orientation can be selected for bone screws having a particular diameter to limit a degree of angular variation when the screw is inserted through the respective aperture. Moreover, the dimensions and directional orientation can be selected to correspond to a particular set of bones. For example, three or more of the apertures can have a different directional orientation to correspond to a different bone. In particular, a bone screw that passes through each aperture can have a trajectory that enables the bone screw to be secured to a corresponding bone in a manner that tends to maximize the purchase of the bone screw to the bone. The bone fusion appliance can be particularly well-suited for fusion of the capitate, hamate, lunate, and triquetrum bones in the carpus (as shown). Similar bone fusion appliances (potentially with different dimensions and having screw apertures that facilitate different directional orientations of bone screws) can be used for fusion of other bones (e.g., tarsus bones). The elongated shape of the bone fusion appliance, along with a relatively narrow lateral dimension, enable the appliance to provide greater exposure to the spaces between the bones to be fused and require less bone resection than prior art circular or diamond-shaped plates.

Figure 1:
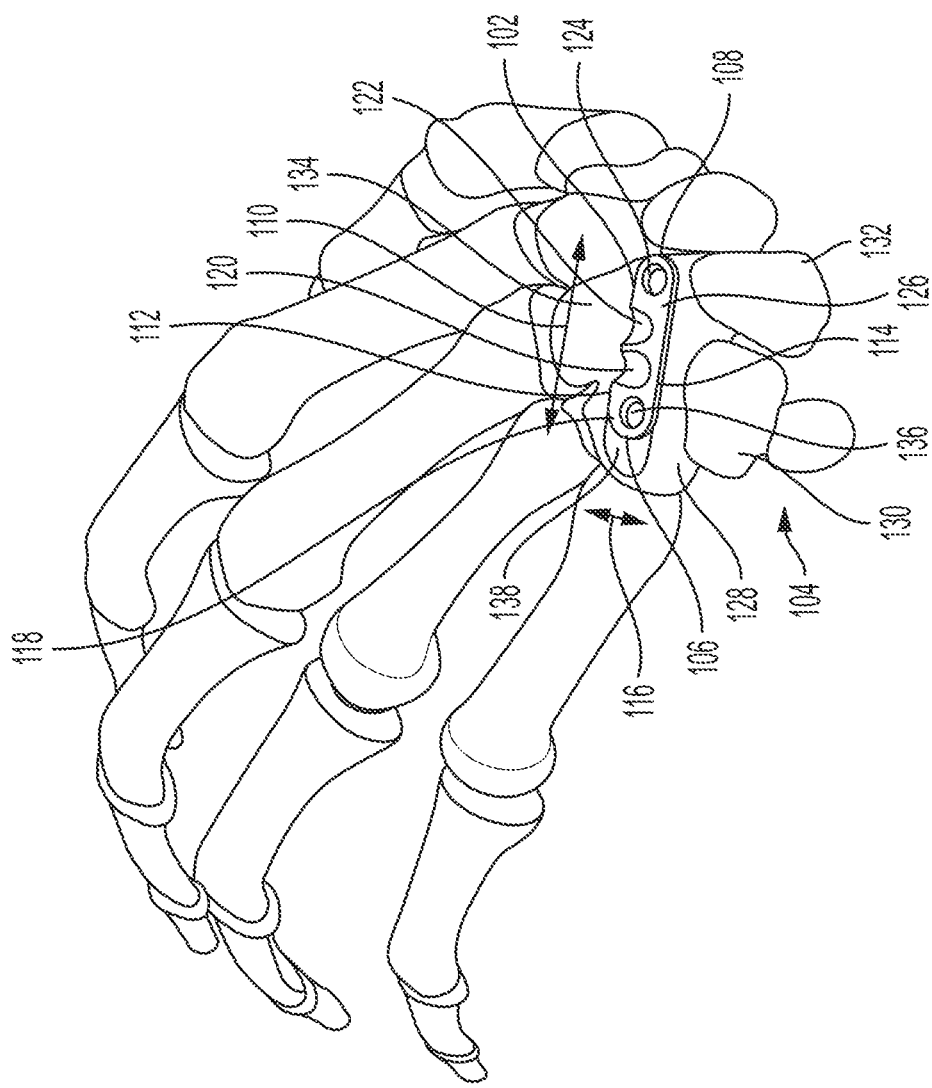
FIG. 1 is a perspective view of a four corner fusion plate implanted on a human carpus.

FIG. 1 is a perspective view of a four corner fusion plate 102 implanted on a human carpus 104. The fusion plate 102 is elongated and has a first end 106 and a second end 108 that correspond to a longitudinal dimension 110 of the fusion plate 102, and a first side 112 and a second side 114 that correspond to a lateral dimension 116 of the fusion plate 102. In general, the longitudinal dimension 110 is significantly greater (e.g., more than twice or more than three times) the lateral dimension 116. The fusion plate 102 includes multiple apertures 118, 120, 122, and 124 that pass through the fusion plate 102 from a top face 126 to a bottom face facing toward the bones of the carpus 104 (see FIGS. 2A-3C). In the illustrated embodiment, each of the apertures corresponds to a particular bone of the carpus 104. In particular, a first aperture 118 corresponds to the hamate 128, a second aperture 120 corresponds to the triquetrum 130, a third aperture 122 corresponds to the lunate 132, and a fourth aperture 124 corresponds to the capitate 134.

The apertures 118, 120, 122, and 124 are situated substantially along a straight line running along the longitudinal dimension 110. In other words, the apertures have approximately the same location in the lateral dimension 116. Situating the apertures in this manner helps maintain a compact size of the fusion plate 102. This advantage can be maintained, however, while allowing some variation from being precisely located along a straight line. In some cases, such a variation may be acceptable or even desirable depending on the target site of a patient. Alternative embodiments may have a sequence of apertures, where each of the apertures has a different location along the longitudinal dimension 110, even if the apertures are not situated substantially along a straight line. The apertures 118, 120, 122, and 124 are also illustrated as being substantially evenly spaced along the longitudinal dimension 110 of the fusion plate 102. Such even spacing of the apertures, however, is not necessarily required. Some implementations may use uneven spacing of the apertures along the longitudinal dimension 110. In general, the fusion plate 102 may be constructed by placing the apertures where they need to be to have best likelihood to purchase into the bone (e.g., in order to drive a screw into a thick portion of the target bone).

Maintaining a compact size of the fusion plate 102 can also be accomplished by constructing the fusion plate 102 such that the lateral dimension 116 is less than three times the diameter of the apertures (e.g. the smallest diameter of an aperture, in cases where the aperture is tapered and/or includes a countersink). In some implementations, the lateral dimension 116 is about twice the diameter of the apertures. These constructions enable the fusion plate 102 to provide an adequate surface for engaging the heads of bone screws that are inserted through the fusion plate 102, sufficient bottom face surface area of the fusion plate 102 to engage the bone(s), and sufficient stiffness and rigidity to fix the bones relative to one another, while remaining relatively compact.

The screw apertures 118, 120, 122, and 124 each have an orientation that enables a bone screw that passes through the aperture (at 136) to be secured to the bone that corresponds to that aperture. The apertures can include a countersink on the top face 126 (as depicted), such that the head of each bone screw does not project above the top face of the plate. The apertures can also include a cylindrical or frusto-conical portion between the countersink and the bottom face through which the shaft of the screw (e.g., the threads and shank, if any) pass. The orientation of each aperture can be defined according to a trajectory of the cylindrical or frusto-conical portion of the aperture. In addition, or as an alternative, the orientation of each aperture can be defined according to an angle of the countersink for that aperture. The apertures may each have a different orientation (e.g., such that the bone screws passing through the different apertures each have a different trajectory). In an alternative implementation, two or more of the apertures (e.g., the aperture 118 corresponding to the hamate 128 and the aperture 124 corresponding to the capitate 134) may have the same or essentially the same orientation.

Figure 3A:
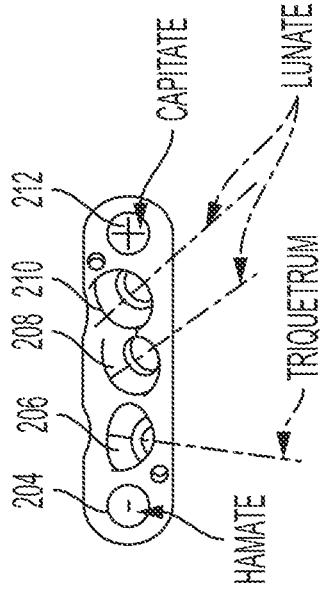
FIGS. 3A, 3B, and 3C are a top plan view, a side view, and an end view, respectively, showing a standard orientation for the screw apertures of the four corner fusion plate shown in FIGS. 2A-2D.
Figure 3C:
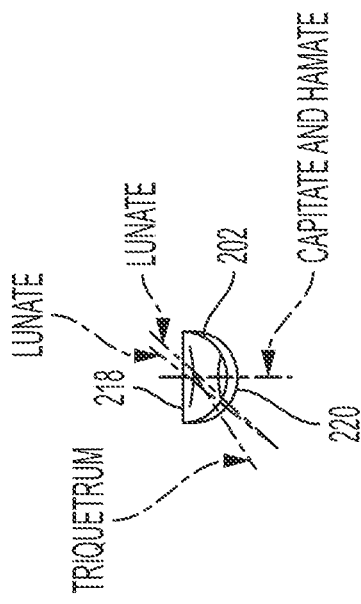
Figure 3B:
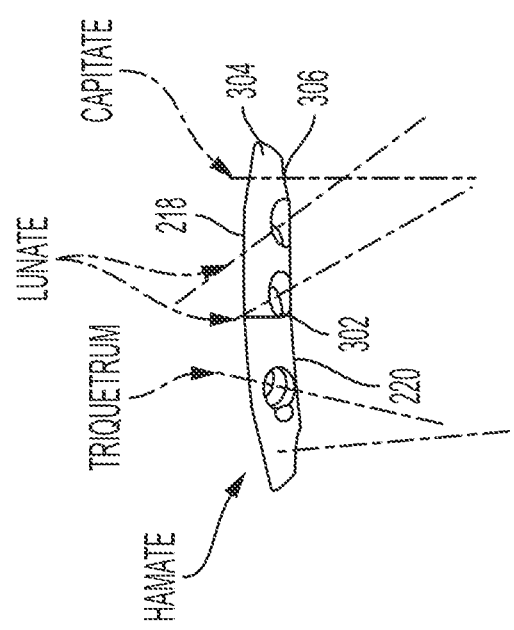

Because the fusion plate 102, as illustrated, is designed to be implanted into the hamate 128 and capitate 134, the orientation of the apertures 118 and 124 (corresponding to the hamate 128 and capitate 134) tend to be substantially perpendicular to the top face 126 of the fusion plate 102, while the apertures 120 and 122 for the triquetrum 130 and lunate 132 tend to be closer to a 45 degree angle to the top face 126 in the lateral direction (see FIGS. 3A-3C). In general, the angles of orientation for the apertures are selected based on where the fusion plate 102 is designed to be located relative to the bones 128, 130, 132, and 134 (or other sets of bones if the fusion plate is designed for an alternative fusion procedure). Thus, the orientation of the apertures may change in particular implementations.

In addition to defining a particular standard orientation, the apertures 118, 120, 122, and 124 may also allow some degree of variation in the trajectory of the bone screws. Such variation enables an orthopedic surgeon, for example, to select a slightly different trajectory based on the patient's bone structure or other factors to provide a more stable attachment and/or improve the ultimate fusion of the bones.

The fusion plate 102 is situated in a channel 138 that is cut (e.g., using a burr) into the hamate 128 and capitate 132 to a sufficient depth so that the top face 126 of the fusion plate 102 is substantially at (or just below) the bone surface to prevent the fusion plate 102 from impinging on soft tissue that overlays the bones. The location where the channel 138 is cut establishes the position where the fusion plate 102 may be implanted. The fusion plate 102 is generally designed to be positioned at a particular location and orientation across the hamate and capitate bones 128 and 134, although some variance from the standard position may be acceptable or even desirable. For example, the position of the fusion plate 102 may be moved longitudinally in the channel 138 (i.e., if the channel is cut longer than the fusion plate 102), the channel 138 may be moved closer to or farther from the triquetrum and lunate bones 130 and 132, the channel 138 may be rotated so that the longitudinal direction is at an oblique angle to the angle of the channel 138 as illustrated in FIG. 1, and/or depth of the channel 138 and thus the fusion plate 102 may be different.

The fusion plate 102 depicted in FIG. 1 includes exactly one screw aperture corresponding to each bone. Alternative embodiments may include a more than one screw aperture for one or more of the bones and may have a different number of apertures corresponding to a different number of bones (e.g., 3 bones or 5 bones) to which the fusion plate can be secured.

Some implementations of the fusion plate may use a different sequence of apertures than that depicted and described in connection with FIG. 1. For example, the position on the fusion plate 102 of the apertures 122 and 124 for the lunate 132 and capitate 134 could be switched, such that the aperture 124 for the capitate 134 is between the apertures 120 and 122 for the triquetrum 130 and the lunate 132. Other sequences of screw apertures may also be possible. Moreover, in cases where more than one aperture is provided for a particular bone, an aperture for one bone (e.g., the capitate) may be between two apertures for another bone (e.g., the lunate). In addition, the sequence of the apertures 118, 120, 122, and 124 is at least partially dependent on whether the fusion plate 102 is for use on the left or right wrist. Thus, a fusion plate 102 for use on the right carpus would generally be a mirror image of a fusion plate 102 for use on the left carpus. In addition, the fusion plate 102 may be offered in different sizes (e.g., 3 or more different sizes) to accommodate different sizes of carpus. The different sizes may be proportionally sized, or may only vary in length (e.g., to enable use of the same sized burr, the same diameter screw, etc.). Similarly, different screw lengths may be provided to account for different sizes of carpus in patients or different depths of penetration into the various bones.

FIGS. 2A, 2B, 2C, and 2D are a perspective view, a top plan view, a side view, and an end view, respectively, of an alternative embodiment of a four corner fusion plate 202. The fusion plate 202 includes five screw apertures, including a first aperture 204 corresponding to the hamate, a second aperture 206 corresponding to the triquetrum, third and fourth apertures 208 and 210 corresponding to the lunate, and a fifth aperture 212 corresponding to the capitate. The use of two screw apertures and thus two screws for the lunate can provide greater stability between the lunate and the capitate (due to the lunate being a fulcrum in which lot of force is placed between the lunate and capitate bones). Each of the apertures 204, 206, 208, 210, and 212 include a countersink 214 and a cylindrical or slightly tapered, frusto-conical portion 216. The countersinks 214 are partially spheroidal and are located on the top face 218 (or dorsal side) of the fusion plate 202, while the cylindrical or frusto-conical portions 216 pass between the countersinks 214 and the bottom face 220 (or volar side) of the fusion plate 202. In cases where a frusto-conical portion is used, the portion 216 may taper either toward or away from the bottom face 220. In other words, the portion 216 may be wider at the intersection 222 with the countersink 214 and narrower at the intersection 224 with the bottom face 220, or vice versa. Such tapering may help facilitate a limited variation in the trajectory of bone screws inserted through the screw apertures.

As shown in FIG. 2D, the fusion plate 202 has a generally flat top face 218 along the lateral dimension and a convexly curved bottom face 220. The flat top face 218 helps the fusion plate 202 substantially conform to the bone surface. The convexly curved bottom face 220 corresponds to a concave channel cut into the bone and may allow for some rotation about the longitudinal axis as the fusion plate 202 is being positioned in the channel. The top face 218 may be highly polished to avoid interfering with soft tissue overlying the fusion plate 202 after implantation. The bottom face 220 may be either smooth or highly textured. A smooth bottom face 220 is easier to position, while a textured or porous bottom face 220 may facilitate better ingrowth and biological fixation. The bottom face 220 may also be treated with a surface deposit to stimulate bone growth such as a hydroxyapatite (HA).

The fusion plate 202 can also include secondary apertures 226 for receiving K-wires to facilitate stabilization of the elongated plate during implantation. In particular, when the fusion plate 202 is located in the desired position, a K-wire can be inserted through each of the secondary apertures and into the underlying bone to temporarily stabilize and hold the fusion plate 202 in place. After one or more bone screws are inserted through the fusion plate 202 and into the bone, the K-wires through the secondary apertures can be removed.

The illustrated fusion plate 202 has a length along the longitudinal dimension of 1.029 (+/−0.005) inches, a width along the lateral dimension of 0.269 (+/−0.005) inches, and a thickness of 0.135 (+/−0.005) inches between the top face 218 and the lowest edge of the bottom face 220. The fusion plate 202 of FIGS. 2B-2D is depicted in proportional dimensions. These dimensions are just one example, however. As discussed above, the fusion plate 202 can be constructed in larger or smaller sizes. The fusion plate 202 can be constructed of a titanium alloy. For example, titanium with 6 parts aluminum and 4 parts vanadium is utilized in a preferred embodiment, although other materials may also be used.

FIGS. 3A, 3B, and 3C are a top plan view, a side view, and an end view, respectively, showing a standard orientation for each of the screw apertures 204, 206, 208, 210, and 212 of the four corner fusion plate 202 shown in FIGS. 2A-2D. The standard orientation corresponds to the base trajectory of a bone screw passing through each screw aperture 204, 206, 208, 210, and 212. As can be seen, the hamate and capitate apertures 204 and 212 are substantially perpendicular to the top face 218 of the fusion plate 202. The orientation of the triquetrum and lunate apertures 206, 208, and 210, on the other hand, have varying x-, y-, and z-components and are all different (i.e., the orientation of the screw apertures and corresponding trajectories of bone screws lie in at least three different planes), although the orientations of the lunate screw apertures 208 and 210 are substantially similar. As discussed above, the orientation of the apertures 204, 206, 208, 210, and 212 is determined based on the standard position for which the fusion plate 202 is designed and the location of the hamate, triquetrum, lunate, and capitate bones relative to that standard position.

In some implementations, the fusion plate 202 can have some longitudinal curvature and/or some variation in thickness or width along the longitudinal dimension. As shown, in FIGS. 2A-2D and 3A-3C, for example, the fusion plate 202 has a slight bend (e.g., of around five degrees) in the middle 302 of the fusion plate 202. In addition, the top face 218 is drafted down at the ends (as shown at 304), and the bottom face 220 is drafted upward at the ends (as shown at 306), resulting in the ends of the fusion plate 202 being tapered when viewed from the side. The bend in the middle and tapering at the ends can help a surgeon implant the top surface of the fusion plate 202 below the bone surface so that soft tissue will not impinge on the fusion plate 202. Although the bend at 302 and the drafting at 304 and 306 are shown as an abrupt change, the fusion plate 202 can also have a more gradual bend or more gradual draft. In addition, although the fusion plate 202 is shown to have substantially the same width along most of the longitudinal dimension, the fusion plate 202 may also be tapered or have other variations in width and thickness. It is appreciated that implementing such features may require altering one or more of trajectories of apertures 201, 206, 208, 210, and 212 with respect to a straight plate in order to correctly direct a screw into a target area.

Figure 4A:
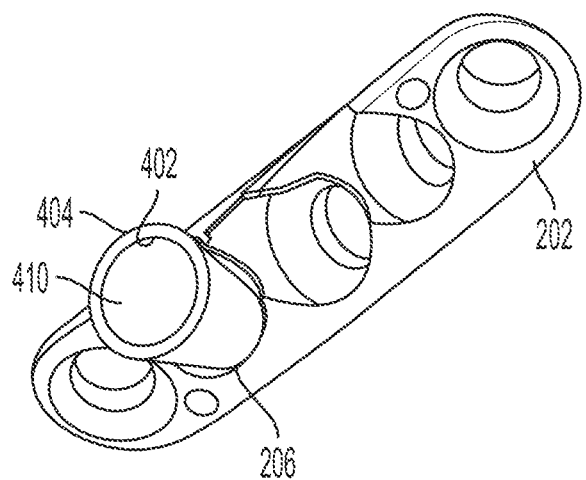
FIGS. 4A and 4B are two perspective views of the fusion plate of FIGS. 2A-3C with a separate drill guide placed into the triquetrum screw aperture.
Figure 4B:
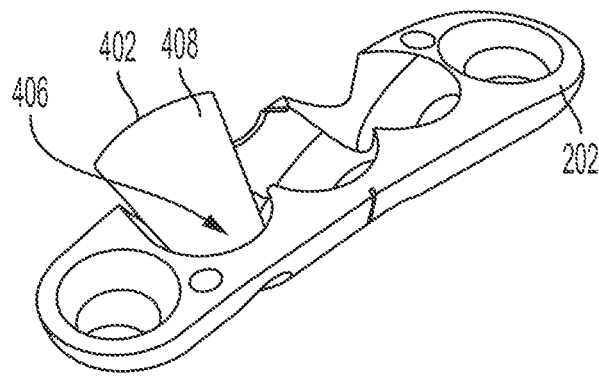

FIGS. 4A and 4B are two perspective views of the fusion plate 202 with a separate drill guide 402 placed into the triquetrum aperture 206. The drill guide 402 has a frusto-conical shape that tapers from a larger diameter at an upper end 404 to a smaller diameter at a lower end 406, although drill guides with a cylindrical shape may also be used. The exterior 408 of the drill guide 402 can be shaped to mate with the apertures (e.g., the countersink 214 and/or portion 216 of FIG. 2) according to the standard orientation of the aperture. The mating may be accomplished by constructing the drill guide 402 so that it screws into the aperture. The inner surfaces 410 of the drill guide 402 are dimensioned to allow a limited amount of variation in the trajectory of a K-wire or drill bit used to designate the path of the bone screw for the aperture. For example, the diameter of the opening at the lower end 406 in cooperation with the inner walls of the drill guide 402 prevent the K-wire or drill bit from being inserted in excess of a predetermined angle in three dimensions (e.g., allowing for +/−10 degrees of angular variability). The drill guide 402 can allow the same amount of angular variation (or angulation) in all directions (e.g., using a right circular frusto-conical shape) or can be shaped to allow a different amount of angular variation for different directions (e.g., using an elliptical and/or oblique frusto-conical shape). In the latter case, the drill guide 402 may also have a preferred orientation for mating with the aperture, which may be dictated by the shape of the drill guide 402 and aperture or indicated by markings on the drill guide 402 and aperture. In some implementations, the same drill guide 402 may be used for some or all of the apertures, while in other implementations, each aperture may have a corresponding drill guide 402 specifically designed for that aperture (e.g., enabling different angulation limits for different apertures).

In some cases, a fusion plate can be provided as part of a kit that includes a number of components for use in implanting the fusion plate. For example, a four corner fusion system kit may include one or more fusion plates (e.g., for left and right and/or for different sized carpi), one or more drill guides, and multiple bone screws. The bone screws may be provided in different lengths but otherwise may be the same diameter so that they are interchangeable between different sizes of fusion plates. The bone screws may be locking screws that have one set of threads along at least a portion of the shaft and another set of threads having a different thread count on or adjacent to a head of the screw. The threads on or adjacent to the screw head can, when tightened into the bone, bite into the countersink of the fusion plate, thereby holding the bone screw at that trajectory and at that depth. Thereafter, if the screw is put under tension, the screw will tend to stay in place. The bone screws can further be cannulated screws to enable each screw to be screwed into the bone over a K-wire that is used to first establish a desired trajectory and location for the bone screw. In some implementations, the bone screws may also be self-tapping or self-drilling screws. At least in the case of self-drilling screws, a drill guide may be unnecessary. Instead, it may be possible to limit angulation of the bone screws based on the dimensions and shape of the screw apertures (e.g., the countersink 214 and/or portion 216 of FIG. 2).

In addition, the four corner fusion system kit can include a burr that is shaped to facilitate cutting into a bone or bones a concave channel for receiving the fusion plate. The burr can be shaped to cut a channel that generally corresponds to, or dovetails with, the shape of the convexly curved bottom face of the fusion plate. The kit can also include a bone preparation guide that can be placed on a bone surface to facilitate proper cutting of the channel with the burr. For example, the bone preparation guide may interface with the carpus to help ensure that the channel is cut in the proper position and orientation. Moreover, the bone preparation guide may help limit the depth of the channel and help ensure that the channel is cut in a generally straight line or other appropriate shape. The kit may further include K-wires for use in establishing the location and trajectory of the bone screws before the bone screws are inserted and a cannulated drill bit for drilling a path for the bone screws into the bone over the K-wires.

Figure 5:
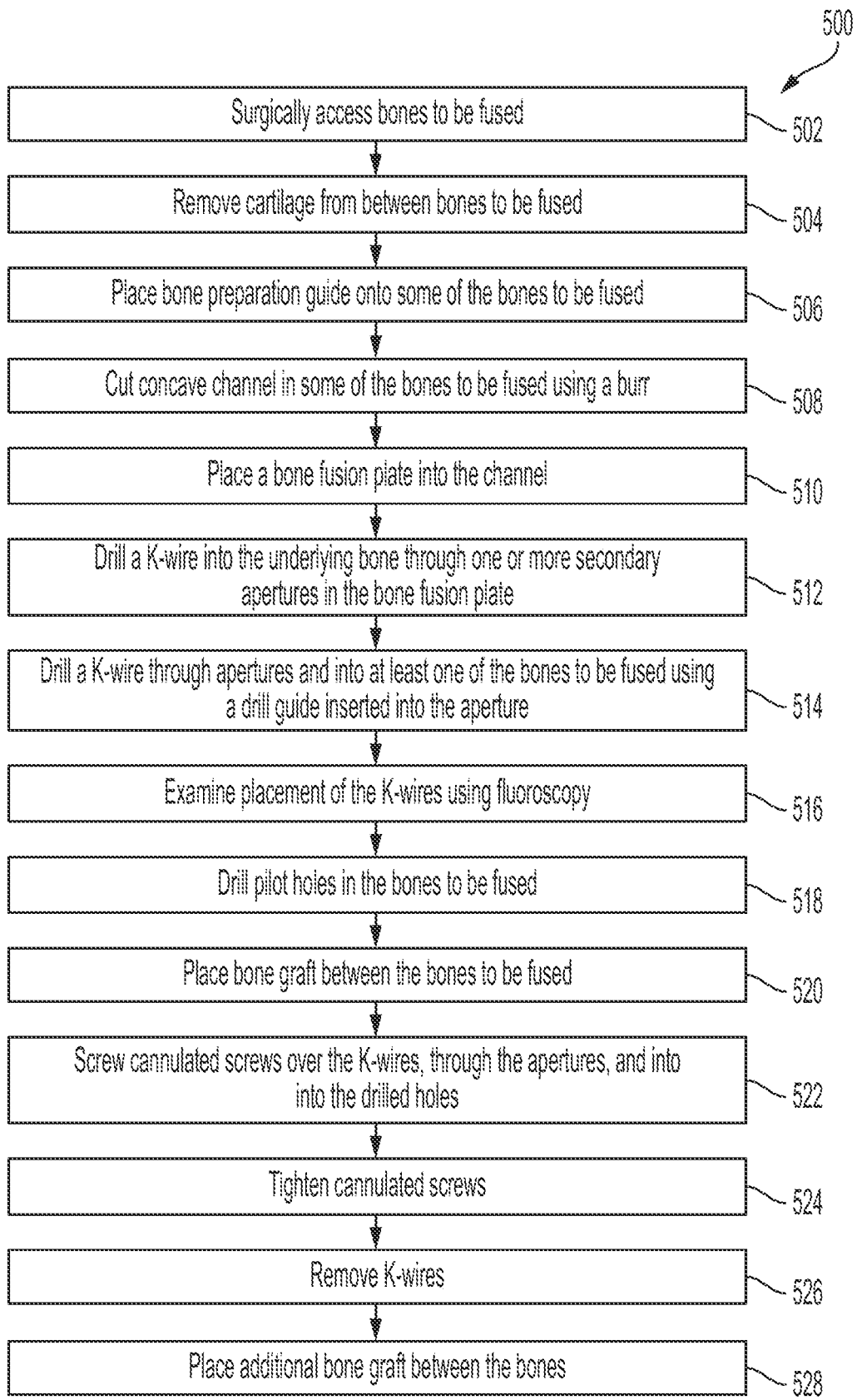
FIG. 5 is a flow diagram of a procedure for implanting a four corner fusion plate.

FIG. 5 is a flow diagram of a procedure 500 for implanting a four corner fusion plate, such as the fusion plates described above. It is appreciated that a claimed method may not require each step of method 500 to be implemented. Further, one or more steps may be implemented in a different order than shown or omitted altogether. The procedure 500 involves surgically accessing the bones to be fused (at 502) and removing cartilage from between the bones to be fused (at 504). A bone preparation guide is placed onto at least a subset of the bones to be fused (at 506). In general, the bone preparation guide provides a guide for drilling a channel in a desired location so that the fusion plate is recessed when it is implanted. A concave channel is cut in at least a subset of the bones to be fused using a burr (at 508). The concave channel may be cut across a portion of lunate and capitate bones. A bone fusion plate is placed into the channel (at 510). One or more K-wires are drilled into the underlying bone through one or more secondary apertures in the bone fusion plate (at 512) to stabilize the bone fusion plate with respect to at least some of the bones to be fused. A K-wire is drilled through each of the apertures and into at least one of the bones to be fused using a frusto-conical drill guide inserted into the screw aperture (at 514). The K-wire provides a pilot hole for the bone screws. The drill guide is configured to limit angulation of the K-wire relative to the bone fusion plate. The placement of the K-wires may be examined, e.g., by using fluoroscopy (at 516), to confirm that the location and trajectory are acceptable. Pilot holes are drilled in the bones to be fused (at 518) using a cannulated drill bit and using the corresponding K-wire to guide the angulation of the pilot hole as it is drilled in the bone. Bone graft may be placed between the bones to be fused (at 520). Cannulated screws are screwed over the K-wires, through the screw apertures, and into the drilled pilot holes (at 522), and the cannulated screws are tightened (at 524) to fixedly stabilize the bones to be fused. The K-wires are removed (at 526) from the secondary apertures and the drilled pilot holes. Additional bone graft may be placed between the bones (at 528).

In general, some of the steps of the procedure may be performed iteratively for different bones. For example, K-wires may be drilled and bone screws inserted into the capitate and lunate bones before drilling K-wires and inserting bone screws into the hamate and triquetrum bones. In some cases, the bone screws are inserted in the order of capitate, lunate, hamate, and triquetrum.

While this specification contains many implementation details, these should not be construed as limitations on the scope of the invention or of what may be claimed, but rather as descriptions of features specific to particular implementations of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking may be advantageous.

Thus, particular implementations of the invention have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

The invention is claimed as follows:

1. A bone fusion system comprising:
   an elongated plate having a top face and a bottom face, and defining a plurality of apertures therethrough;
   the elongated plate having a longitudinal dimension between a first end and a second end and having a lateral dimension between a first side and a second side;
   each aperture of the plurality of apertures arranged along the longitudinal dimension of the elongated plate, wherein the plurality of apertures comprises:

a first aperture having a first orientation and is configured to correspond to a first bone, a second aperture having a second orientation and is configured to correspond to a second bone, and a third aperture having a third orientation and is configured to correspond to a third bone, wherein the second aperture is disposed between the first aperture and the third aperture, wherein the first bone, the second bone, and the third bone are selected from a group consisting of a capitate bone, a hamate bone, a lunate bone, and a triquetrum bone, wherein the first bone, the second bone, and the third bone are different from each other, wherein at least two of the first, second, and third orientations are different from each other.

2. The bone fusion system of claim 1, wherein the bottom face of the elongated plate has a convexly curved surface between the first and second sides of the elongated plate.

3. The bone fusion system of claim 1, wherein the bottom face of the elongated plate has a smooth surface.

4. The bone fusion system of claim 1, wherein the bottom face of the elongated plate has a textured surface.

5. The bone fusion system of claim 4, wherein the treatment of the bottom face comprises depositing a hydroxyapatite.

6. The bone fusion system of claim 1, wherein the bottom face of the elongated plate is treated with a surface deposit.

7. The bone fusion system of claim 1, wherein the top face of the elongated plate has a flat surface across the lateral dimension.

8. The bone fusion system of claim 1, wherein the top face of the elongated plate has a polished surface.

9. The bone fusion system of claim 1, wherein the first and third orientations are the same.

10. The bone fusion system of claim 9, wherein the elongated plate defines a longitudinal axis extending along the longitudinal dimension, wherein the first and third orientations are substantially perpendicular to the longitudinal axis.

11. The bone fusion system of claim 1, further comprising a fourth aperture having a fourth orientation.

12. The bone fusion system of claim 11, wherein the fourth aperture is disposed between the second aperture and the third aperture, wherein the fourth orientation of the fourth aperture is different from the second orientation of the second aperture.

13. The bone fusion system of claim 12, wherein the fourth aperture is configured to correspond to the second bone.

14. The bone fusion system of claim 12, wherein the elongated plate defines a longitudinal axis extending along the longitudinal dimension, wherein at least one of the second and fourth orientations is substantially at a forty five degree angle to the longitudinal axis.

15. The bone fusion system of claim 12, wherein the top face of the elongated plate is drafted down near the first end and the second end.

16. The bone fusion system of claim 11, wherein the fourth orientation of the fourth aperture is the same as the second orientation of the second aperture.

17. The bone fusion system of claim 11, wherein the orientation of the first aperture and the fourth aperture tend to be substantially perpendicular to the top face of the elongated plate, wherein the second aperture and the third aperture tend to be closer to a 45 degree angle to the top face in the lateral direction.

18. The bone fusion system of claim 1, wherein each of the first, second, and third apertures has a countersink, wherein the first, second, and third orientations of the first, second, and third apertures are defined by an angle of the countersink of the first, second, and third apertures, respectively.

19. The bone fusion system of claim 1, further comprising a fifth aperture having a fifth orientation and is configured to correspond to a fourth bone different from the first, second, and third bones, wherein the fifth aperture is disposed between the first aperture and the second aperture, wherein the fifth orientation is different from the first, second, and third orientations.

20. The bone fusion system of claim 1, wherein a different directional orientation corresponds to a different bone.

* * * * *